United States Patent [19]

Watts

[11] 4,410,535
[45] Oct. 18, 1983

[54] AZA-BICYCLO-BENZAMIDE DERIVATIVES AND PHARMACEUTICAL COMPOSITIONS AND USE THEREOF

[75] Inventor: Eric A. Watts, Harlow, England

[73] Assignee: Beecham Group Limited, England

[21] Appl. No.: 325,978

[22] Filed: Nov. 30, 1981

[30] Foreign Application Priority Data

Dec. 12, 1980 [GB] United Kingdom ............... 8039823

[51] Int. Cl.³ .................... A61K 31/46; C07D 451/04
[52] U.S. Cl. ...................................... 424/265; 548/124
[58] Field of Search .......................... 546/124; 424/265

[56] References Cited

U.S. PATENT DOCUMENTS

| | | | |
|---|---|---|---|
| 4,273,778 | 6/1981 | Hadley et al. | 424/265 |
| 4,336,259 | 6/1982 | Hadley et al. | 424/265 |
| 4,350,691 | 9/1982 | Hadley et al. | 546/124 X |

Primary Examiner—Richard Raymond
Attorney, Agent, or Firm—Jacobs & Jacobs

[57] ABSTRACT

Compounds of the formula (I) and pharmaceutically acceptable salts thereof:

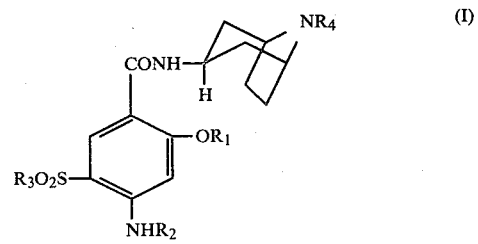

wherein:
  $R_1$ is $C_{1-6}$ alkyl;
  $R_2$ is hydrogen or $C_{1-7}$ acyl;
  $R_3$ is $C_{1-6}$ alkyl;
  $R_4$ is a group $CH_2R_5$ wherein $R_5$ is hydrogen, $C_{3-8}$ cycloalkyl or phenyl optionally substituted by one or two substituents selected from $C_{1-6}$ alkyl, $C_{1-4}$ alkoxy, trifluoromethyl and halogen, having useful anti-emetic activity.

8 Claims, No Drawings

AZA-BICYCLO-BENZAMIDE DERIVATIVES AND PHARMACEUTICAL COMPOSITIONS AND USE THEREOF

This invention relates to substituted benzamides having useful pharmacological activity, to pharmaceutical compositions containing them and processes for their preparation.

Published European Patent Application No. 79302978.6 and U.S. Pat. No. 4,273,778 each disclose compounds of formula (A):

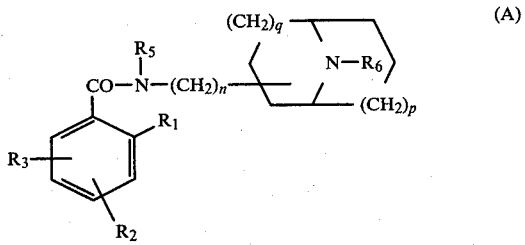

wherein:

$R_1$ is a $C_{1-6}$ alkoxy group;

$R_2$ and $R_3$ are the same or different and are hydrogen, halogen, $CF_3$, $C_{2-7}$ acyl, $C_{2-7}$ acylamino, or amino, aminocarbonyl or aminosulphone optionally substituted by one or two $C_{1-6}$ alkyl groups, $C_{1-6}$ alkylsulphone or nitro;

$R_5$ is hydrogen or $C_{1-6}$ alkyl;

$R_6$ is $C_{1-7}$ alkyl or a group $-(CH_2)_sR_7$ where s is 0 to 2 and $R_7$ is a $C_{3-8}$ cycloalkyl group, or a group $-(CH_2)_tR_8$ where t is 1 or 2, and $R_8$ is $C_{2-5}$ alkenyl or a phenyl group optionally substituted by one or two substituents selected from $C_{1-6}$ alkyl, $C_{1-4}$ alkoxy, trifluoromethyl and halogen; and n, p and q are independently 0 to 2.

Depending on their balance between peripheral and central action, the compounds of the formula (A) are disclosed as useful in the treatment of disorders related to impaired gastro-intestinal motility, emesis, and/or in the treatment of disorders of the central nervous system.

Compounds wherein $R_6$ contains five or more carbon atoms, particularly benzyl and wherein the aromatic nucleus is 4-amino-5-chloro-2-methoxy substituted are described as of particular interest for their anti-emetic and CNS activity.

We have surprisingly found a hitherto not specifically disclosed small group of compounds having good anti-emetic activity coupled with a high specificity of action. These compounds have an advantageous therapeutic ratio (based on CNS effects) over the best and the structurally closest anti-emetic compounds specifically disclosed in European application No. 79302978.6 and U.S. Pat. No. 4,273,778.

Accordingly, the present invention provides compounds of the formula (I) and pharmaceutically acceptable salts thereof:

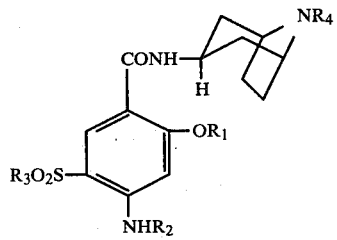

wherein:

$R_1$ is $C_{1-6}$ alkyl;

$R_2$ is hydrogen or $C_{1-7}$ acyl;

$R_3$ is $C_{1-6}$ alkyl;

$R_4$ is a group $CH_2R_5$ wherein $R_5$ is hydrogen, $C_{3-8}$ cycloalkyl or phenyl optionally substituted by one or two substituents selected from $C_{1-6}$ alkyl, $C_{1-4}$ alkoxy, trifluoromethyl and halogen.

Suitable examples of $R_1$ include methyl, ethyl, n- and iso-propyl groups. Preferably $R_1$ is methyl.

Suitable examples of $R_2$ include hydrogen and $C_{1-6}$ alkanoyl, such as formyl, acetyl, propionyl, n- and iso-butyryl groups. More suitably $R_2$ is hydrogen or a formyl or acetyl group. Preferably $R_2$ is hydrogen.

Suitable examples of $R_3$ include methyl, ethyl, n- and iso-propyl groups. Preferably $R_3$ is a methyl or ethyl group, in particular methyl.

Suitable examples of $R_5$ when a $C_{3-8}$ cycloalkyl group include $C_{5-8}$ cycloalkyl, preferably cyclohexyl. When $R_5$ is an optionally substituted phenyl group as hereinbefore defined, suitable examples of such optional phenyl substituents include methyl, ethyl, n- and iso-propyl, n, sec and tertbutyl; methoxy, ethoxy, n- and iso-propoxy; $CF_3$, fluoro, chloro, and bromo. Preferably $R_5$, when optionally substituted phenyl, is unsubstituted.

Preferably, therefore, $R_4$ is benzyl.

The pharmaceutically acceptable salts of the compounds of the formula (I) include acid addition salts with conventional acids such as hydrochloric, hydrobromic, phosphoric, sulphuric, citric, tartaric, lactic and acetic acid.

The pharmaceutically acceptable salts of the compounds of the formula (I) also include quaternary ammonium salts. Examples of such salts include such compounds quaternised by compounds such as $R_9$-Y wherein $R_9$ is $C_{1-6}$ alkyl, phenyl $-C_{1-6}$ alkyl or $C_{5-7}$ cycloalkyl, and Y is an anion of an acid. Suitable examples of $R_9$ include methyl, ethyl and n- and iso-propyl; and benzyl and phenethyl. Suitable examples of Y include the halides such as chloride, bromide and iodide.

Examples of pharmaceutically acceptable salts also include internal salts such as N-oxides.

The compounds of the formula (I) can also form hydrates.

In the compound of formula (I) it will be seen that the $-CO-NH-$ linkage has $\beta$ orientation with respect to the nortropane ring, that is:

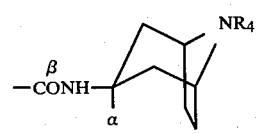

A group of compounds within formula (I) consists of those wherein $R_5$ is other than hydrogen.

A favoured group of compounds within formula (I) is of formula (II) and pharmaceutically acceptable salts thereof;

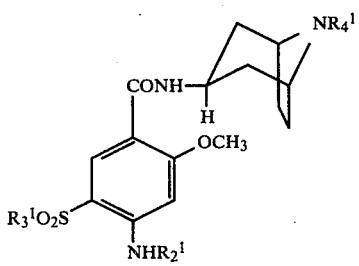

wherein:
$R^1_2$ is hydrogen or a formyl or acetyl group;
$R^1_3$ is methyl or ethyl;
$R^1_4$ is a group $CH_2R^1_5$, wherein
$R^1_5$ is as optionally substituted phenyl group as defined in formula (I).
Preferably $R^1_2$ is hydrogen.
Preferably $R^1_3$ is methyl.
Suitable examples of $R^1_5$ are as hereinbefore described under formula (I) for $R_5$ when optionally substituted phenyl.
Preferably $R^1_5$ is unsubstituted phenyl.
Preferably, therefore $R^1_4$ is benzyl.
A preferred compound of this invention, therefore, is: 4-amino-2-methoxy-5-methylsulphonyl-N-[3-β-(8-benzyl-8-azabicyclo[3.2.1]octyl)]benzamide.

A group of compounds of interest within formula (I) is of formula (III) and pharmaceutically acceptable salts thereof:

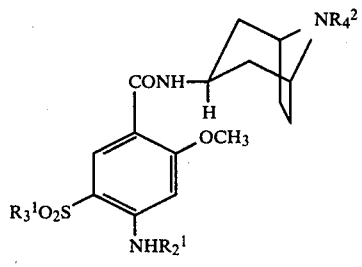

wherein:
$R^1_2$ and $R^1_3$ are as defined in formula (II);
$R^2_4$ is a group $CH_2R^2_5$ wherein $R^2_5$ is $C_{3-8}$ cycloalkyl.
Preferably $R^1_2$ us hydrogen.
Preferably $R^1_3$ is methyl.
Suitable and preferred examples of $R^2_5$ are as hereinbefore described under formula (I) for $R_5$ when $C_{3-8}$ cycloalkyl.
Two further compounds of interest are 4-amino-2-methoxy-5-methylsulphonyl-N-[3β-(8-methyl-8-azabicyclo[3.2.1] octyl)]benzamide and 4-amino-2-methoxy-5-ethylsulphonyl-N-[3β-(8-methyl-8-azabicyclo[3.2.1]octyl)]benzamide, especially the former.

It will, of course, be realised that the compounds of the formula (I) have a prochiral centre, and thus other stereoisomeric forms outside formula (I) exist. The compounds of formula (I) may be separated from the other isomeric forms by the usual methods, or may be obtained by stereospecific synthesis.

The invention also provides a process for the preparation of a compound of formula (I) which process comprises reacting an acid of the formula (IV) or a reactive derivative thereof;

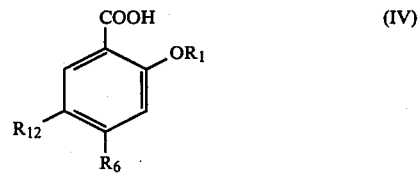

wherein
$R_1$ is as defined in formula (I);
$R_6$ is amino, protected amino or nitro; and
$R_{12}$ is $C_{1-6}$ alkylsulphonyl, $C_{1-6}$ alkylsulphinyl or $C_{1-6}$ alkylthio; with a compound of formula (V):

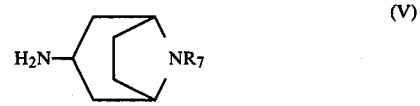

wherein $R_7$ is $R_4$ as defined or a hydrogenolysable protecting group; and thereafter if necessary converting $R_{12}$ to $R_3SO_2$, converting a group $R_6$ to $NHR_2$, and, if desired or necessary, converting a group $R_2$ in the resulting compound of formula (I) to another group $R_2$, converting $R_7$ to $R_4$, and optionally forming a pharmaceutically acceptable salt of the resultant compound of the formula (I).

Examples of N-protecting groups in $R_6$ include $C_{1-6}$ alkanoyl, for example acetyl, propionyl n- and isobutyryl and 2,2-dimethylpropanoyl, benzoyl or benzene optionally substituted in the phenyl ring by one or two substituents selected from $C_{1-4}$ alkyl, $C_{1-4}$ alkoxy, trifluoromethyl, halogen or nitro; and $C_{1-4}$ alkoxycarbonyl, for example tert-butoxycarbonyl.

Suitable examples of $R_7$ protecting groups include those listed above for N-protecting groups in $R_6$ which are hydrogenolysable.

'Reactive derivative' when used herein means a derivative of the compound (IV) which can be reacted with the compound (V) to form an amido linkage between the acid group of the compound (IV) and the amino group of the compound of the formula (V).

Often this reactive derivative will be the acid halide, such as the acid chloride, of the acid (IV). In such cases, the reaction will normally be carried out in an inert solvent, preferably in the presence of an acid acceptor. The inert solvent can be any solvent inert to both reactants, such as benzene, toluene, diethyl ether or the like. The acid acceptor is suitably an organic base such as a tertiary amine e.g. triethylamine, trimethylamine, pyridine or picoline, or an inorganic acid acceptor, such as calcium carbonate, sodium carbonate, potassium carbonate or the like. It should also be noted that it is possible to use certain acid acceptors as the inert solvent, for example organic bases.

The reaction may also be carried out by forming an anhydride of the acid (IV) in the usual manner from ethyl chloroformate and reacting that with the compound (V); normally a conventional mixed anhydride will be used; or by reacting the acid (IV) and the compound (V) in the presence of a dehydrating catalyst such as a carbodiimide, for example dicyclohexylcarbodiimide.

These reactions may be carried out at any nonextreme temperature such as −10° to 100° C. and more suitably 0° to 80° C. The higher reaction temperatures are employed with less active acids whereas the lower temperatures are employed with the more reactive acids.

The reaction will normally be carried out in a nonhydroxylic solvent, inert to both reactants such as benzene, toluene or diethyl ether.

The reactive derivatives may be a highly activated ester, such as the pentachlorophenyl ester, when ambient temperatures may be used. The reaction is generally effected in an inert polar solvent, such as dimethylformamide.

Conversion of $R_6$ protected amino to amino may be effected conventionally.

When $R_6$ is $C_{1-6}$ alkanoyl-amino or optionally substituted benzoyl-amino as defined conversion to amino is conveniently effected by conventional base hydrolysis.

When $R_6$ is $C_{1-4}$ alkoxycarbonyl-amino or optionally substituted benzyl-amino as defined, conversion to amino may be carried out conventionally, for example by hydrogenolysis. Suitable reactions are conventional transition—metal catalysed hydrogenation, using for example palladium—or platinum—charcoal, at atmospheric pressure or a slight excess thereover. A dry, inert, polar solvent such as dry ethanol and ambient temperatures are apt.

$R_6$ nitro groups may be converted to amino groups by conventional methods, such as reduction with metals in acid solution, for example with tin and hydrochloric acid.

Conversion of $R_7$ to $R_4$ may be carried out by deprotection and subsequent reaction with $R_4Q$ wherein Q is a group or atom readily displaced by a nucleophile.

Suitable values for Q include chloride, bromide, iodide, $OSO_2CH_3$ or $OSO_2.C_6H_5.p.CH_3$.

Favoured values for Q include chloride, bromide and iodide.

De-protection may suitably be effected as described above for hydrogenolysable protected amino $R_6$, under conventional conditions.

The reaction of the de-protected product with $R_4Q$ may be carried out under conventional alkylation conditions, for example, in an inert solvent such as dimethylformamide in the presence of an acid acceptor such as potassium carbonate. Generally the reaction is carried out at a non-extreme temperature such as at ambient or at a slightly elevated temperature.

In the preparation of the compounds of the invention it is preferred that $R_6$ is $R_4$ as in the desired compound of formula (I). It will be appreciated that where $R_4$ is sensitive to reaction steps to intermediates it is preferred to use an inert group $R_7$ during such steps, and to convert it to $R_4$ subsequently as described above.

It will be appreciated that interconversions of $R_6$ or $R_7$ may take place in any desired or necessary order. The skilled man will appreciate that protection of an $NHR_2$ amino group with a group such as trityl may be necessary when converting hydrogen to an $R_4$ group.

$R_{12}$ $C_{1-6}$ alkylthio or $C_{1-6}$ alkylsulphinyl may be converted to $R_3SO_2$ as defined, by oxidation.

These oxidations may conveniently be carried out conventionally at below ambient temperatures using an organic peracid in a non-aqueous inert reaction medium preferably a chlorinated hydrocarbon solvent, for example using 3-chloroperbenzoic acid, or using a water soluble inorganic strong oxidant, such as an alkali metal permanganate, periodate or hydrogen peroxide in aqueous solution.

Such an oxidation on a compound of the formula (I) may also form the N-oxide of the bicyclic moiety therein.

Given the specific substitution desired and having been decided whether the compound or its N-oxide is required, the skilled man will readily ascertain whether such interconversion is desirable.

In general however it is more convenient to prepare a compound of formula (I) from the corresponding $C_{1-6}$ alkylsulphonyl acid or its reactive derivative.

Any conversion of $R_{12}$, $R_6$ or $R_7$ may take place in any desired or necessary order.

It will be realised that in the compound of the formula (I) the —CO—NH— linkage has a $\beta$ orientation with respect to the nortropane ring to which it is attached. A mixture of $\alpha$ and $\beta$ isomers of the compound of the formula (I) may be synthesized nonstereospecifically and the desired isomer separated conventionally therefrom, e.g. by chromatography; or alternatively the $\beta$ isomer may, if desired, by synthesized from the corresponding $\beta$ form of the compound of the formula (V).

Synthesis from the corresponding $\beta$ isomer of the compound of the formula (V) is in general preferred.

The $\beta$ form of the compound of formula (V) may, if desired, be prepared by known stereospecific processes, such as those leading to the $\beta$ isomers of the compound of formula (V), for example as described in Published European Application No. 4,273,778 and U.S. Pat. No. 4,273,778.

The acid addition salts of the compounds of the formula (I) may be prepared in entirely conventional manner by reacting a compound of the formula (I) in base form with the chosen acid.

The quaternary ammonium salts of the compounds of the formula (I) may be prepared in conventional manner for such salts, such as by reaction of the chosen compound of the formula (I) with a compound $R_9Y$ as defined. This reaction is suitably carried out in an appropriate solvent such as acetone, methanol, ethanol, dimethylformamide, at ambient or raised temperature and pressure.

The nitrogen atom of the nortropane moiety may also form an N-oxide to give an internal N-oxide salt of the compound of the formula (I). The N-oxides may be prepared in conventional manner such as by reaction of the chosen compound of the formula (I) with an organic per-acid such as m-chloroperbenzoic acid. This reaction is suitably carried out at below ambient temperature in an organic solvent, preferably a chlorinated hydrocarbon solvent.

The intermediates of the formulae (IV) and (V) are either known compounds or can be prepared by analogous processes to known compounds. For example, intermediates of formula (IV) wherein $R_6$ is $NH_2$ may be prepared according to the following reaction sequence:

Scheme 1

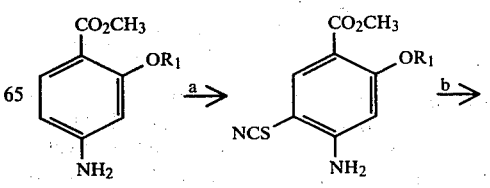

-continued
Scheme 1

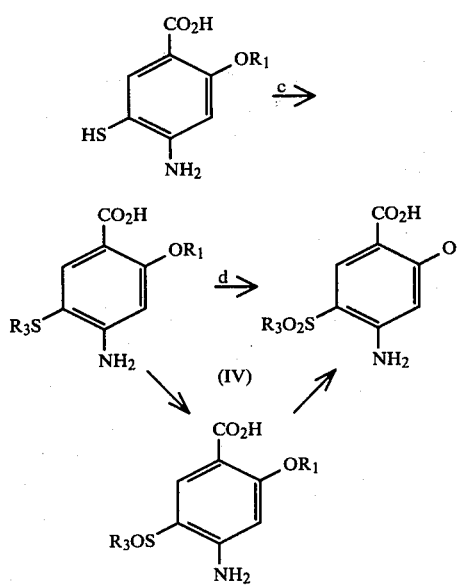

Process steps a to d inclusive are illustrated hereinafter with reference to parts (a) to (d) respectively of the description for preparation of intermediates to the Examples.

Introduction of the functional group $R_{12}$ can also be achieved by chlorosulphonation followed by reduction, basic cleavage, alkylation and optional oxidation as shown in scheme 2:

disulphide, which may be hydrolysed by heating with 10% sodium hydroxide solution to give a thiol. The thiol can be reacted in situ with an alkylating agent such as a dialkyl sulphate resulting in the formation of the alkyl sulphide (IVA). If desired partial or complete oxidation of the alkylthio derivatives (IVA) is effected. Suitable reagents for these oxidations include hydrogen peroxide and acetic acid; sodium periodate or potassium hydrogen persulphate. Other methods which may be used to form the alkyl sulphides (IVA) include the treatment of acids of formula (VI) with perchloric acid, phosphonyl chloride and dialkyl sulphoxide to form the corresponding sulphonium salts, subsequently dealkylated.

Scheme 3

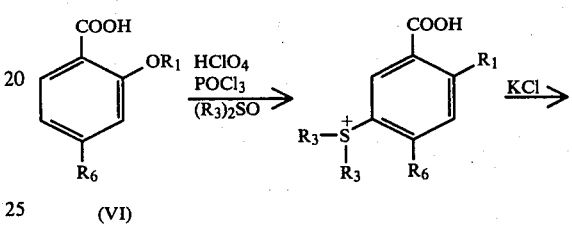

Scheme 2

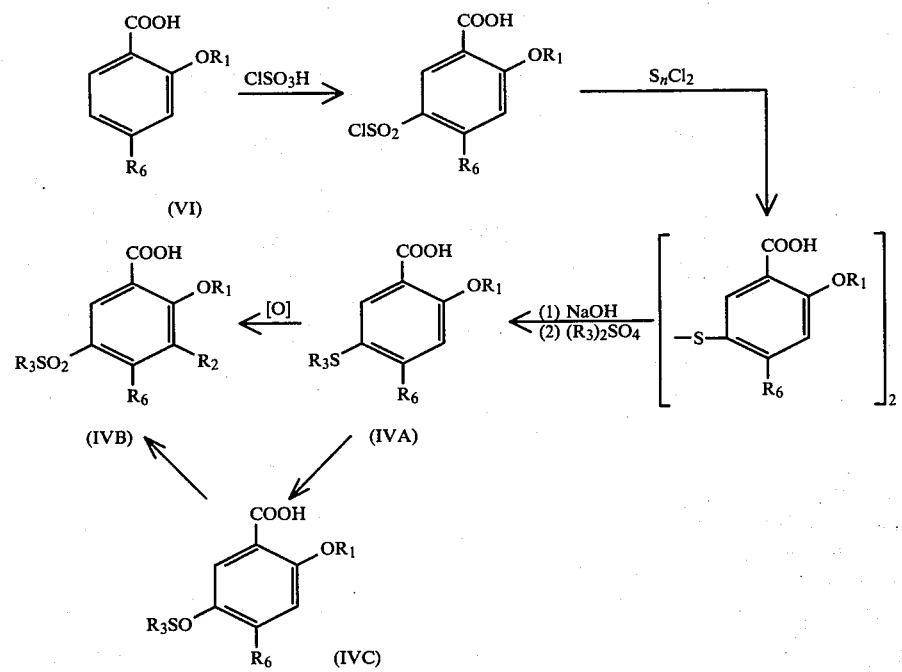

The process of chlorosulphonation involves reacting chlorosulphonic acid with an acid of formula (VI) to give the corresponding chlorosulphonyl derivative with tin (II) chloride in hydrochloric acid will give the Intermediates of formula (V) may be prepared as described in published European patent application No. 79302978.6, or U.S. Pat. No. 4,273,778.

It will be realised that compounds of formulae (VI) and (VII):

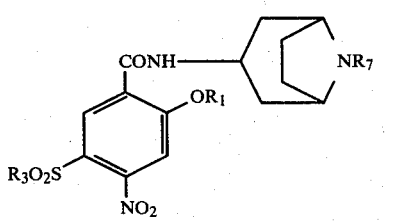
(VI)

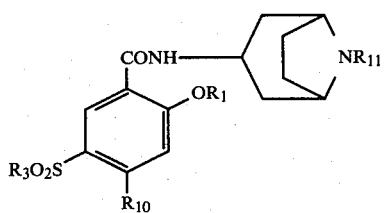
(VII)

wherein $R_1$, $R_3$ and $R_7$ are as hereinbefore defined, $R_{10}$ is amino or protected amino and $R_{11}$ is hydrogen or a hydrogenolysable N-protecting group are useful novel intermediates, and as such form an aspect of the invention.

The compounds of the formula (I) are particularly useful in the treatment of emesis, because they combine a high level of anti-emetic activity with a good therapeutic ratio (based on CNS effects). It is also noted that the compounds have gastric-motility enhancing activity, which it is believed will additionally enhance their usefulness as anti-emetics.

The invention, therefore, also provides a pharmaceutical composition comprising a compound of the formula (I), or a hydrate or a pharmaceutically acceptable salt thereof, together with a pharmaceutically acceptable carrier. Such compositions may be adapted for oral or parenteral administration, and as such may be in the form of tablets, capsules, oral liquid preparations, powders, granules, lozenges, reconstitutable powders, injectable and infusable solutions or suspensions; the compositions may also favourably be in the form of suppositories, particularly when an oral formulation may not be advisable, such as in the treatment of cancer patients. Normally, orally administrable compositions are preferred.

Tablets and capsules for oral administration may be in unit dose presentation form, and may contain conventional excipients such as binding agents, fillers, tabletting lubricants, disintegrants, and acceptable wetting agents and the like. The tablets may be coated according to methods well known in normal pharmaceutical practice. Oral liquid preparations may be in the form of, for example, aqueous or oily suspensions, solutions, emulsions, syrups, or elixirs, or may be presented in a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavouring or colouring agents.

For parenteral administration, fluid unit dosage forms are prepared utilizing the compound of the formula (I) and a sterile vehicle. The compound, depending on the vehicle and concentration used, can be either suspended or dissolved in the vehicle. In preparing solutions the compound can be dissolved for injection and filter sterilized before filling into a suitable vial or ampoule and sealing. Advantageously, adjuvants such as a local anaesthetic, preservatives and buffering agents can be dissolved in the vehicle. Parenteral suspensions are prepared in substantially the same manner except that the compound is suspended in the sterile vehicle. Advantageously, a surfactant or wetting agent is included in the composition to facilitate uniform distribution of the compound.

As is common practice, the compositions will usually be accompanied by written or printed directions for use in the medical treatment concerned.

It will, of course, be realised that the precise dosage used in the treatment of any of the hereinbefore described disorders will depend on the actual compound of the formula (I) used, and also on other factors such as the seriousness of the disorder being treated.

The invention further provides a method of treatment of emesis and/or disorders related to impaired gastrointestinal motility in animals including humans comprising the administration of an effective amount of a compound of the formula (I) or a pharmaceutically acceptable salt thereof. The "effective amount" will depend in the usual way on a number of factors such as the nature and severity of the malady to be treated, the weight of the sufferer, and the actual compound used.

However, by way of illustration, unit doses will suitably contain 0.01 to 100 mgs of the compounds of formula (I) more suitably from 0.01 to 50 mgs, for example 0.02 to 20 mgs.

Again by way of illustration, such unit doses will suitably be administered more than once a day, for example 2, 3, 4, 5 or 6 times a day, in such a way that the total daily dose is suitably in the range 0.01 to 10 mg/kg per day.

Compounds of the formula (I) have the ability to potentiate the effect of conventional analgesics in migraine treatment when administered concurrently with the analgesic.

Thus the invention provides a pharmaceutical composition comprising a compound of the formula (I) and an analgesic.

The compound of the formula (I) and the analgesic, such as aspirin or paracetamol, will be present in the composition in amounts generally similar to their usual effective dose.

The composition can be a combination product, for example a tablet or capsule containing both a compound of the the formula (I) and an analgesic for oral administration, or a twin pack comprising the two active ingredients made up for separate administration.

The invention accordingly provides a method of treatment of migraine comprising the administration to the sufferer of a compound of the formula (I) and an analgesic.

The following Example illustrates the preparation of the compounds of formula (I) and the following Description illustrates the preparation of intermediates thereto.

DESCRIPTION

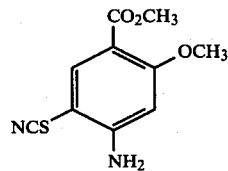 (a)

Methyl-4-amino-2-methoxybenzoate (25.0 g, 0.138 mole) was dissolved with warming in dry methanol (150 ml), cooled to 0°–5° and treated with potassium thiocyanate (27 g) Bromine (7.5 ml) in dry methanol (100 ml) was added dropwise with stirring. After 3 hours following addition the reaction mixture was poured into water (1 L). The colourless precipitate was filtered, washed with water, dried in vacuo and recrystallised from ethyl acetate to give methyl-4-amino-2-methoxy-5-thiocyano benzoate (25.0 g, 78%) mp 188°–189°.

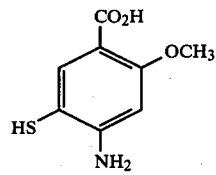 (b)

Methyl-4-amino-2-methoxy-5-thiocyano benzoate (10 g, 0.042 mole) was dissolved in ethanol (100 ml) and water (100 ml) containing NaOH (4 g), and heated to reflux 85°–90° C. for 7 hours. The mixture was cooled, evaporated in vacuo to ½ volume, cooled and acidified. The resulting solid was filtered and dried to give 4-amino-2-methoxy-5-mercaptobenzoic acid (7.13 g, 86%).

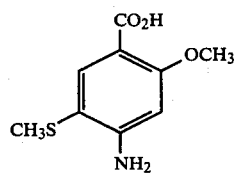 (c)

4-amino-5-mercapto-2-methoxybenzoic acid (7.13 g, 0.036 mole) was dissolved with boiling in dilute sodium hydroxide (144 mg 2.5 N) and water (100 ml). The solution was cooled and treated with dimethyl sulphate (ca. 6 g) and left to stand 24 hours. The mixture was made thoroughly alkaline by addition of dilute sodium hydroxide (10 mls) and boiled for 15 minutes. The cooled solution was acidified with dilute hydrochloric acid and extracted with chloroform (3×150 ml). The combined extracts were dried (MgSO₄) filtered and evaporated in vacuo to give 4-amino-2-methoxy-5-methylthiobenzoic acid (4.35 g 57%) mp. 151°–2° C.

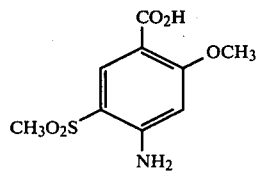 (d)

4-amino-2-methoxy-5-methylthiobenzoic acid (1.3 g, 0.0061 mole) was dissolved in warm glacial acetic acid (5.5 ml) cooled to 35° and treated with 100 volume hydrogen peroxide (3 ml) dropwise. The temperature rose to 80° C., then fell to ca. 40° C. The mixture was maintained at 40° C. for 3 hours, then cooled to 10° C. to give 4-amino-2-methoxy-5-methylsulphonylbenzoic acid (0.70 g 62%) mp. 214° C.

EXAMPLE 1

4-Amino-2-methoxy-5-methylsulphonyl-N-[3-β-(8-benzyl-8-azabicyclo[3.2.1]octyl)]benzamide (1)

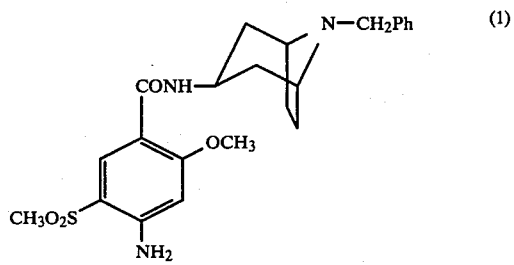

4-amino-2-methoxy-5-methylsulphonyl-benzoic acid (0.70 g, 0.00285 mole) was dissolved in acetone (30 ml) containing triethylamine (0.89 g) and cooled to 0°–5° C.

Ethyl chloroformate (0.31 g) was added dropwise over 15 mins. and the reaction mixture left to stir at 0° for a further 15 mins. 3-β-Amino(8-benzyl-8-azabicyclo[3.2.1]octane) (0.61 g) was added in one portion and the reaction mixture was allowed to reach ambient temperatures over 24 hours.

The reaction mixture was evaporated in vacuo, the residue was dissolved in water basified with dilute sodium hydroxide and extracted with chloroform (3×80 ml). The combined organic extracts were dried (MgSO₄) filtered and evaporated in vacuo. The residual oil was chromatographed on Kieselgel 60 (Art 7734) using 10% methanol in chloroform to yield. 4-amino-2-methoxy-5-methylsulphonyl-N-[3-β-(8-benzyl-8-azabicyclo-[3.2.1]octyl)]benzamide. (0.60 g 50%) as colourless crystals mp. 208°–210° C. ex. ether.

$C_{23}H_{29}N_3O_4S$ requires C=62.30, H=6.54, N=9.48 found C=62.25, H=6.58, N=9.27

EXAMPLE 2

4-Amino-5-ethylsulphonyl-2-methoxy N-[3-β-(8-benzyl-8azabicyclo{3,2,1}octyl)]benzamide (2)

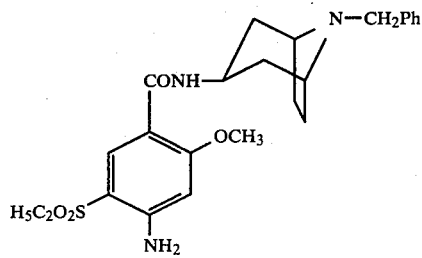

4-Amino-5-ethylsulphonyl-2-methoxybenzoic acid (1.67 g, 0.0065 mole) was dissolved in anhydrous amine-free dimethyl formamide (30 ml) containing triethylamine (0.65 g, 0.9 ml). The solution was cooled to 0° and ethylchloroformate (0.70 g, 0.62 ml) added dropwise maintaining the temperature between 0° and 3°. After a further 10 minutes 3amino-8-benzyl-8azabicyclo{3,2,-

1}octane (1.39 g, 0.0065 mole) was added in dimethylformamide (5 ml) and the reaction allowed to warm to ambient temperatures overnight.

The mixture was evaporated to dryness in vacuo and treated with water (15 ml), dilute sodium hydroxide (10 ml 2.5 N) and extracted with chloroform (3×100 ml). The combined extracts were dried (Na$_2$SO$_4$) filtered and evaporated in vacuo. The resulting semi-solid was chromatographed on Kieselgel 7734 using ethyl acetate as eluant to give the title compound as colourless solid on trituration with dry ether. Yield 1.0 g 35% mp 204°–5° C.

$C_{24}H_{31}N_3O_4S = 457$ Requires C=63.02 H=6.78 N=9.19 S=7.00 Found C=63.23 H=6.98 N=9.18 S=6.78 Calculated mass 457.2031 Observed 457.2024

4-Amino-2-methoxy-5-methylsulphonyl-N-[3β-(8-methyl-8-azabicyclo[3.2.1]octyl)]benzamide (3) was prepared analogously.

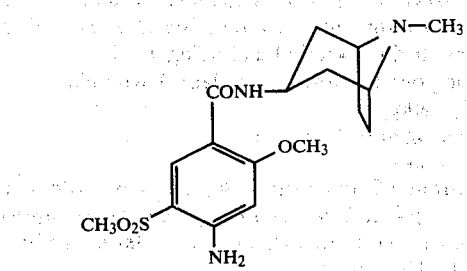

(1.0 g, 20%) as a colourless crystalline solid mp 193°–195° C.

$C_{17}H_{25}N_3O_4S$. Required C=55.58 H=6.81 N=11.44 S=8.72 Found C=55.24 H=6.79 N=11.11 Calculated Mass 367.1566 observed 367.1553.

4-acetamido-2-methoxy-5-methylsulphonyl-N-[3β-(8-benzyl-8-azabicyclo[3.2.1]octyl]benzamide (4) is prepared analogously.

EXAMPLE 3

4-Amino-2-methoxy-5-methylsulphonyl-N-{3-β-[8-(4-chlorobenzyl)-8-azabicyclo(3.2.1)octyl]}benzamide (5)

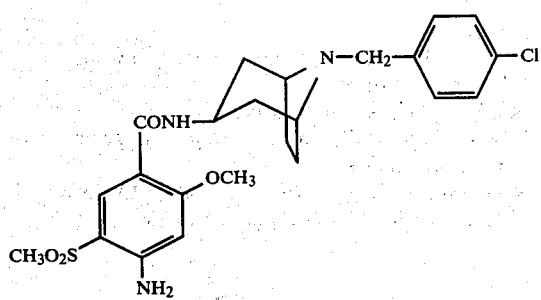

4-Amino-5-methylsulphonyl-2-methoxy-N-[3β-(8-benzyl-8-azabicyclo{3,2,1}octyl)]benzamide (as prepared in Example 1) (2.215 g, 0.005 mole) was hydrogenated over 10% Pd/C in ethanol/dimethylformamide (100 ml; 2:1) until H$_2$ uptake had ceased (ca. 150 ml).

The catalyst was removed by filtration through kieselguhr and the filtrate evaporated in vacuo (176 g). The residue was redissolved in dry dimethylformamide (50 ml) and treated with 4-chlorobenzylchloride (0.81 g) in the presence of potassium carbonate (ca. 1.5 g) and a crystal of potassium iodide. The mixture was heated to 80°–90° C. for 18 hours, filtered and evaporated in vacuo. The residue was chromatographed on Kieselgel 60 (Art 7734) via chloroform containing 5–10% methanol, to yield the title compound as colourless microcrystals (1.15 g, 50%) m.p. 236°–237° C.

$C_{23}H_{28}ClN_3O_4S$ Requires % C=57.80 H=5.86 N=8.80 Cl=7.43. Found % C=57.55 H=5.84 N=8.66 Cl=7.53

The following were prepared analogously:

4-Amino-2-methoxy-5-methylsulphonyl-N-{3-β-[8-(4-methoxybenzyl)-8-azabicyclo(3.2.1)octyl]}benzamide (6)

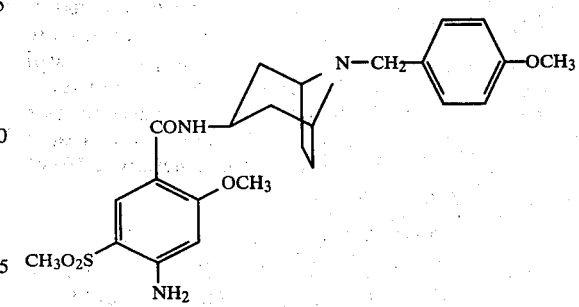

(50%) mp 201°–202°.

$C_{24}H_{31}N_3O_5S = 473$ Mass Spectral Analysis. Observed mass 473.1972 Calculated 473.1981.

4-Amino-2-methoxy-5-methylsulphonyl-N-{3-β-[8-(4-fluorobenzyl)-8-azabicyclo(3.2.1)octyl]}benzamide (7)

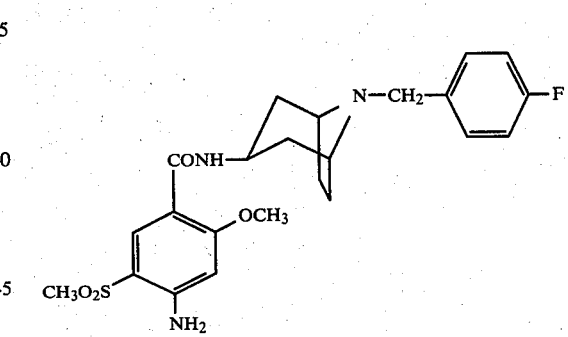

4-amino-2-methoxy-5-methylsulphonyl-N-{3β-[8-(4-methylbenzyl)-8-azabicyclo(3.2.1)octyl]}benzamide (8)

4-amino-2-methoxy-5-methylsulphonyl-N-{3β-[8-(3-trifluoromethylbenzyl)-8-azabicyclo(3.2.1)octyl]}benzamide (9), 4-amino-2-methoxy-5-methylsulphonyl-N-{3β-[8-cyclohexylmethyl)-8-azabicyclo(3.2.1)octyl]}benzamide (10) are prepared analogously.

Pharmacological Data

I. Anti-emetic acitivity in the dog

Compounds were administered subcutaneously 30 minutes prior to administration of a standard dose of apomorphine HCl (0.1 mg/kg subcutaneously) and the vomiting response compared to that obtained when the same animals were dosed with apomorphine HCl and vehicle only.

II. Dopamine Receptor Blocking Activity in the Central Nervous System

Compounds were tested for inhibition of apomorphine induced climbing in the mouse. The test is based on that described by Protais, P., Constantin, J. and Schwartz J. C. (1976), Psychopharmacology, 50, 1–6.

Apomorphine 1 mg/kg s.c. induces mice to climb the wall of a wire cage (inverted food hopper—11×7.5×18 cm high). Mice acclimatised in their home cages in groups of 5 are placed under the hoppers immediately after the injection of apomorphine 1 mg/kg s.c. At 10,20 and 30 minutes after injection climbing behaviour is scored. The mice are observed for 30 seconds and scored according to the position they spend the majority of time in, score 0—four paws on floor of cage; score 1—fore paws only on walls; score 2—all paws on wall of cage. The scores at all 3 times and for each mouse are summed and mice drug treated orally compared to mice receiving apomorphine only. A saline only treated group is also included and any score, generally <5% of maximum taken into account.

III. Gastric Motility Testing in the rat

The compounds were tested for ability to reverse the inhibitory effect of 6,7-ADTN on gastric motility as recorded by an open tipped catheter in the conscious chronic gastric fistula rat. Administration of 1 mg/kg s.c. of 6,7-ADTN reduced basal gastric motor activity and this was reversed by the administration of 0.008 mg/kg s.c. of compound 1. administered 10 minutes after the 6,7-ADTN. Control injections did not reverse the inhibition. For subcutaneous testing the compound was dissolved in water by the addition of tartaric acid (½ mole per mole of compound).

Comparison Testing and General Pharmacology

The tests I and II shown above for anti-emetic and CNS activity respectively were used for the comparison testing of representative Compound 1 with 4-amino-5-chloro-2-methoxy-N-(3'β-[8'-benzyl]-8-azabicyclo[3.2.1]octyl)benzamide (A'). Compound A' was chosen because of the compounds specifically disclosed in European Patent Application No. 793029978 and U.S. Pat. No. 4,273,778 it has the best anti-emetic activity and is the structurally closest compound to compound 1. Other compounds of the Examples were also submitted to tests I and II.

The results are shown in Table 1.

TABLE 1

| Compound | Anti-emetic activity (ED$_{50}$) | CNS activity (ED$_{50}$) |
|----------|----------------------------------|--------------------------|
| 1        | 0.002                            | 3.5                      |
| A'       | 0.0005                           | 0.0029                   |
| 2        | 0.01                             | 3.5                      |
| 3        | 0.5                              | 80                       |

All figures mg/kg s.c.

These results clearly show that the therapeutic ratio for anti-emetic activity based upon CNS effects is more than 300 times better for Compound 1 compared with compound A', and at least 30 times better for other compounds tested.

Toxicity

No toxic effects were observed in any of the above tests.

I claim:

1. A compound of the formula (I) and pharmaceutically acceptable salts thereof:

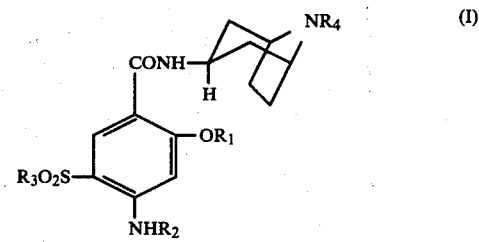

wherein:
R$_1$ is C$_{1-6}$ alkyl;
R$_2$ is hydrogen or C$_{1-7}$ acyl;
R$_3$ is C$_{1-6}$ alkyl;
R$_4$ is a group CH$_2$R$_5$ wherein R$_5$ is hydrogen, C$_{3-8}$ cycloalkyl or phenyl optionally substituted by one or two substituents selected from C$_{1-6}$ alkyl, C$_{1-4}$ alkoxy, trifluoromethyl and halogen.

2. A compound according to claim 1 wherein:
R$_1$ is C$_{1-6}$ alkyl;
R$_2$ is hydrogen or C$_{1-7}$ acyl;
R$_3$ is C$_{1-6}$ alkyl;
R$_4$ is a group CH$_2$R$_5$ wherein R$_5$ is C$_{3-8}$ cycloalkyl or phenyl optionally substituted by one or two substituents selected from C$_{1-6}$ alkyl, C$_{1-4}$ alkoxy, trifluoromethyl and halogen.

3. A compound according to claim 2 of formula (II) or a pharmaceutically acceptable salt thereof:

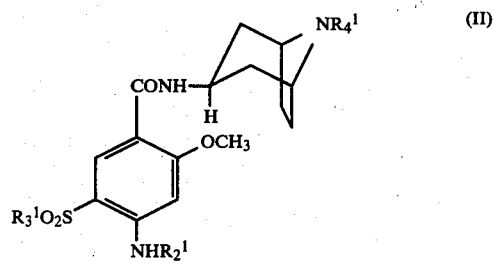

wherein:
R$^1_2$ is hydrogen or a formyl or acetyl group;
R$^1_3$ is methyl or ethyl;
R$^1_4$ is a group CH$_2$R$^1_5$, wherein
R$^1_5$ is as optionally substituted phenyl group as defined in claim 1.

4. A compound according to claim 2 of formula (III) or a pharmaceutically acceptable salt thereof:

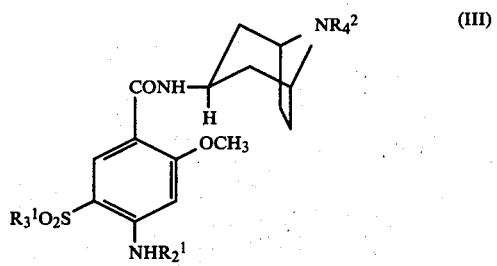

wherein:
R$^1_2$ and R$^1_3$ are as defined in claim 3;
R$^2_4$ is a group CH$_2$R$^2_5$ wherein $R_5^2$ is $C_{3-8}$ cycloalkyl.

5. A compound according to claim 1 which is 4-amino-2-methoxy-5-methylsulphonyl-N-[3β-(8-methyl-8-azabicyclo[3.2.1]octyl)]benzamide or 4-amino-2-methoxy-5-ethylsulphonyl-N-(3β-(8-methyl-8-azabicyclo[3.2.1]octyl)]-benzamide or a pharmaceutically acceptable salt thereof.

6. A compound according to claim 1 which is 4-amino-2-methoxy-5-methylsulphonyl-N-[3-β-(8-benzyl-8-azabicyclo[3.2.1]octyl)]benzamide, 4-amino-2-methoxy-5-methylphonyl-N-[3β-(8-benzyl-8-azabicyclo[3.2.1]-octyl]benzamide,4-amino-2-methoxy-5-methylsulphonyl-N-{3-β-[8-(4-chlorobenzyl)-8-azabicyclo(3.2.1)octyl]}-benzamide, 4-amino-2-methoxy-5-methylsulphonyl-N-{3-β-[8-(4-methoxybenzyl)-8-azabicyclo(3.2.1)octyl]}benzamide, 4-amino-2-methoxy-5-methylsulphonyl-N-{3-β-[8-(4-fluorobenzyl)-8-azabicyclo(3.2.1)octyl]}benzamide, 4-amino-2-methoxy-5-methylsulphonyl-N-{3β-[8-(4-methylbenzyl)-8-azabicyclo(3.2.1)octyl]}benzamide, 4-amino-2-methoxy-5-methylsulphonyl-N-{3β-[8-(3-trifluoromethylbenzyl)-8-azabicyclo(3.2.1)octyl]}benzamide, 4-amino-2-methoxy-5-methylsulphonyl-N-{3β-[8-cyclohexylmethyl)-8-azabicyclo(3.2.1)octyl]}benzamide or a pharmaceutically acceptable salt thereof.

7. A pharmaceutical composition useful in the treatment of emesis and/or disorders related to impaired gastrointestinal motility, comprising an effective amount of a compound according to claim 1 or a hydrate or a pharmaceutically acceptable salt thereof, together with a pharmaceutically acceptable carrier.

8. A method of treatment of animals including humans suffering from emesis and/or disorders related to impaired gastro-intestinal motility, comprising the administration to the sufferer of an effective amount of a compound according to claim 1 or a pharmaceutically acceptable salt thereof.

\* \* \* \* \*